United States Patent
Nakano et al.

(10) Patent No.: US 10,962,516 B2
(45) Date of Patent: Mar. 30, 2021

(54) AMMONIA SENSOR ELEMENT AND GAS SENSOR

(71) Applicant: NGK SPARK PLUG CO., LTD., Nagoya (JP)

(72) Inventors: Yoshihiro Nakano, Komaki (JP); Tetsuo Yamada, Komaki (JP)

(73) Assignee: NGK SPARK PLUG CO., LTD., Aichi (JP)

(*) Notice: Subject to any disclaimer, the term of this patent is extended or adjusted under 35 U.S.C. 154(b) by 11 days.

(21) Appl. No.: 16/297,919

(22) Filed: Mar. 11, 2019

(65) Prior Publication Data
US 2019/0302077 A1 Oct. 3, 2019

(30) Foreign Application Priority Data
Mar. 27, 2018 (JP) .............................. JP2018-059399

(51) Int. Cl.
| | |
|---|---|
| G01N 27/404 | (2006.01) |
| G01N 33/00 | (2006.01) |
| G01N 27/419 | (2006.01) |
| F01N 11/00 | (2006.01) |
| F01N 3/20 | (2006.01) |
| G01N 27/407 | (2006.01) |

(52) U.S. Cl.
CPC ....... *G01N 33/0054* (2013.01); *F01N 3/2066* (2013.01); *F01N 11/007* (2013.01); *G01N 27/4045* (2013.01); *G01N 27/4075* (2013.01); *G01N 27/419* (2013.01); *G01N 33/0037* (2013.01); *F01N 2560/021* (2013.01); *F01N 2560/026* (2013.01); *F01N 2610/02* (2013.01)

(58) Field of Classification Search
CPC .......... G01N 27/4045; G01N 27/4075; G01N 33/0054
See application file for complete search history.

(56) References Cited

U.S. PATENT DOCUMENTS

2011/0048970 A1* 3/2011 Sugaya ................ G01N 27/419
                                                        205/781
2014/0060012 A1    3/2014 Kakimoto
(Continued)

FOREIGN PATENT DOCUMENTS

| JP | 2005083817 A * | 3/2005 | ............ G01N 27/12 |
| JP | 2011-075546 A | 4/2011 | |
| JP | 2013-221931 A | 10/2013 | |

(Continued)

OTHER PUBLICATIONS

EPO machine-generated English language translation of the Description section of Kakimoto et al. JP 2005083817 A (Year: 2005).*

*Primary Examiner* — Alexander S Noguerola
(74) *Attorney, Agent, or Firm* — Sughrue Mion, PLLC (57) ABSTRACT

Disclosed is an ammonia sensor element for detecting ammonia in a gas under measurement, including two mixed-potential-type ammonia detection cells that respectively include first and second ammonia detection electrodes. The first ammonia detection electrode has a metal composition containing Au as a predominant component. The second ammonia detection electrode has a metal composition containing Au as a predominant component. The metal compositions of the first and second ammonia detection electrodes are different from each other.

7 Claims, 7 Drawing Sheets

(56) References Cited

U.S. PATENT DOCUMENTS

| | | |
|---|---|---|
| 2015/0013431 A1 | 1/2015 | Kakimoto et al. |
| 2016/0356199 A1 | 12/2016 | Kakimoto |

FOREIGN PATENT DOCUMENTS

| | | |
|---|---|---|
| JP | 2014-062541 A | 4/2014 |
| JP | 2015-034814 A | 2/2015 |
| JP | 6088463 B2 | 3/2017 |

\* cited by examiner

AMMONIA SENSOR ELEMENT AND GAS SENSOR

FIELD OF THE INVENTION

The present invention relates to an ammonia sensor element and a gas sensor equipped with an ammonia sensor element. Hereinafter, the term "front" refers to a gas sensing side with respect to the axial direction of a gas sensor (sensor element); and the term "rear" refers to a side opposite the front side.

BACKGROUND OF THE INVENTION

In recent years, attention has been focused on urea selective catalytic reduction (SCR) systems as a technique to purify nitrogen oxides (NOx) contained in exhaust gases of internal combustion engines such as diesel engines. The urea SCR system is configured to purify nitrogen oxides (NOx) contained in the exhaust gas by converting the nitrogen oxides to nitrogen ($N_2$) through chemical reaction of the nitrogen oxides with ammonia ($NH_3$). There is a possibility that, when an excessive amount of ammonia is supplied to the nitrogen oxides in the urea SCR system, unreacted ammonia remaining in the exhaust gas will be released to the outside. In order to prevent such ammonia release, the urea SCR system is equipped with an ammonia sensor element to measure the concentration of ammonia in the exhaust gas as disclosed in e.g. Japanese Laid-Open Patent Publication No. 2015-34814, Japanese Laid-Open Patent Publication No. 2011-75546, Japanese Laid-Open Patent Publication No. 2013-221931 and Japanese Laid-Open Patent Publication No. 2014-62541.

SUMMARY OF THE INVENTION

In view of the fact that the ammonia sensor element is used under exposure to harsh vehicle exhaust gas environment, there has been a demand to develop an ammonia sensor element that utilizes a novel ammonia detection technique so as to withstand various usage environments.

Further, a protection layer is optionally formed on a detection electrode of the ammonia sensor element so as to protect the detection electrode from water and poisoning substance. The detection electrode is generally predominantly composed of Au, which is low in catalytic activity, and is consequently low in melting point so that evaporation or melting of the electrode material may occur during sintering. The protection layer thus needs to be formed by low-temperature sintering or thermal spraying, which makes it difficult to ensure sufficient strength and poisoning resistance of the protection layer.

The present invention has been made under the foregoing circumstances. It is a first object of the present invention to provide an ammonia sensor element which utilizes a novel ammonia detection technique and to provide a gas sensor with such an ammonia gas sensor. It is a second object of the present invention to provide an ammonia sensor element which has a protection layer with sufficient strength and poisoning resistance and to provide a gas sensor with such an ammonia gas sensor.

The present invention can be embodied in the following forms.

In accordance with a first aspect of the present invention, there is provided an ammonia sensor element for detecting ammonia in a gas under measurement, comprising two mixed-potential-type ammonia detection cells that respectively include first and second ammonia detection electrodes, wherein the first ammonia detection electrode has a metal composition containing Au as a predominant component, wherein the second ammonia detection electrode has a metal composition containing Au as a predominant component, and wherein the metal compositions of the first and second ammonia detection electrodes are different from each other.

In this aspect, the first and second ammonia detection electrodes are of different metal compositions from each other as mentioned above, whereby the ammonia sensor element enables accurate separation and detection of ammonia from NOx in the gas under measurement.

Herein, the expression "different metal compositions" include the following cases: (1) where the metal compositions contain different components; (2) where the metal compositions contain the same components at different ratios; and (3) where the metal compositions contain different components at different ratios.

In accordance with a second aspect of the present invention, there is provided an ammonia sensor element as described above, wherein the ammonia detection cells are integrally covered with a protection layer or separately covered with protection layers, wherein the metal composition of the first ammonia detection electrode contains a metal having a melting point higher than that of Au and capable of alloying with Au, and wherein the metal composition of the second ammonia detection electrode contains a metal having a melting point higher than that of Au and capable of alloying with Au.

The ammonia detection cell is optionally covered with a protection layer so as to protect the ammonia detection electrode from water and poisoning substance. When the detection electrode is predominantly composed of Au (low in catalytic activity), however, the melting point of the detection electrode is low so that evaporation or melting of the electrode material may occur during sintering. The protection layer thus needs to be formed by low-temperature sintering or thermal spraying, which makes it difficult to ensure sufficient strength and poisoning resistance of the protection layer. In order to impart sufficient strength and poisoning resistance to the protection layer, it has been required to form the protection layer by high-temperature sintering. In this aspect, each of the metal compositions of the first and second ammonia detection electrode contains a metal having a higher melting point than Au and capable of alloying with Au as mentioned above. With the addition of such alloying metals, the melting points of the first and second ammonia detection electrodes are raised. It is thus possible to form the protection layer with sufficient strength and poisoning resistance by the adoption of high-temperature sintering.

In accordance with a third aspect of the present invention, there is provided an ammonia sensor element as described above, wherein the metal composition of the first ammonia detection electrode consists of an alloy phase of Au and Pt, and wherein the metal composition of the second ammonia detection electrode consists of an alloy phase of Au and Pd.

In this aspect, the ammonia sensor element enables more accurate detection of ammonia and attains more improvement in the strength and poisoning resistance of the protection layer.

In accordance with a fourth aspect of the present invention, there is provided an ammonia sensor element as described above, wherein the metal composition of the first ammonia detection electrode has a weight ratio Pt/(Au+Pt) of 0.05 to 0.25, and wherein the metal composition of the second ammonia detection electrode has a weight ratio Pd/(Au+Pd) of 0.04 to 0.20.

In this aspect, the ammonia sensor element reliably ensures sufficient output for practical use.

In accordance with a fifth aspect of the present invention, there is provided an ammonia sensor element as described above, wherein the metal composition of the first ammonia detection electrode has a weight ratio Pt/(Au+Pt) of 0.10 to 0.20, and wherein the metal composition of the second ammonia detection electrode has a weight ratio Pd/(Au+Pd) of 0.06 to 0.15.

In this aspect, the ammonia sensor element more reliably ensures sufficient output for practical use.

In accordance with a sixth aspect of the present invention, there is provided a gas sensor, comprising the above-described ammonia sensor element.

In this aspect, the gas sensor enables accurate separation and detection of ammonia from NOx in the gas under measurement.

In accordance with a seventh aspect of the present invention, there is provided a gas sensor as described above, wherein the gas sensor is in the form of a multi-gas sensor comprising a NOx sensor part that measures the concentration of nitrogen oxides in the gas under measurement.

In this aspect, the gas sensor enables accurate separation and detection of ammonia and NOx.

The other objects and features of the present invention will also become understood from the following description.

DESCRIPTION OF EMBODIMENTS

Hereinafter, an exemplary embodiment of the present invention will be described below with reference to FIGS. 1 to 10.

Figure 1:
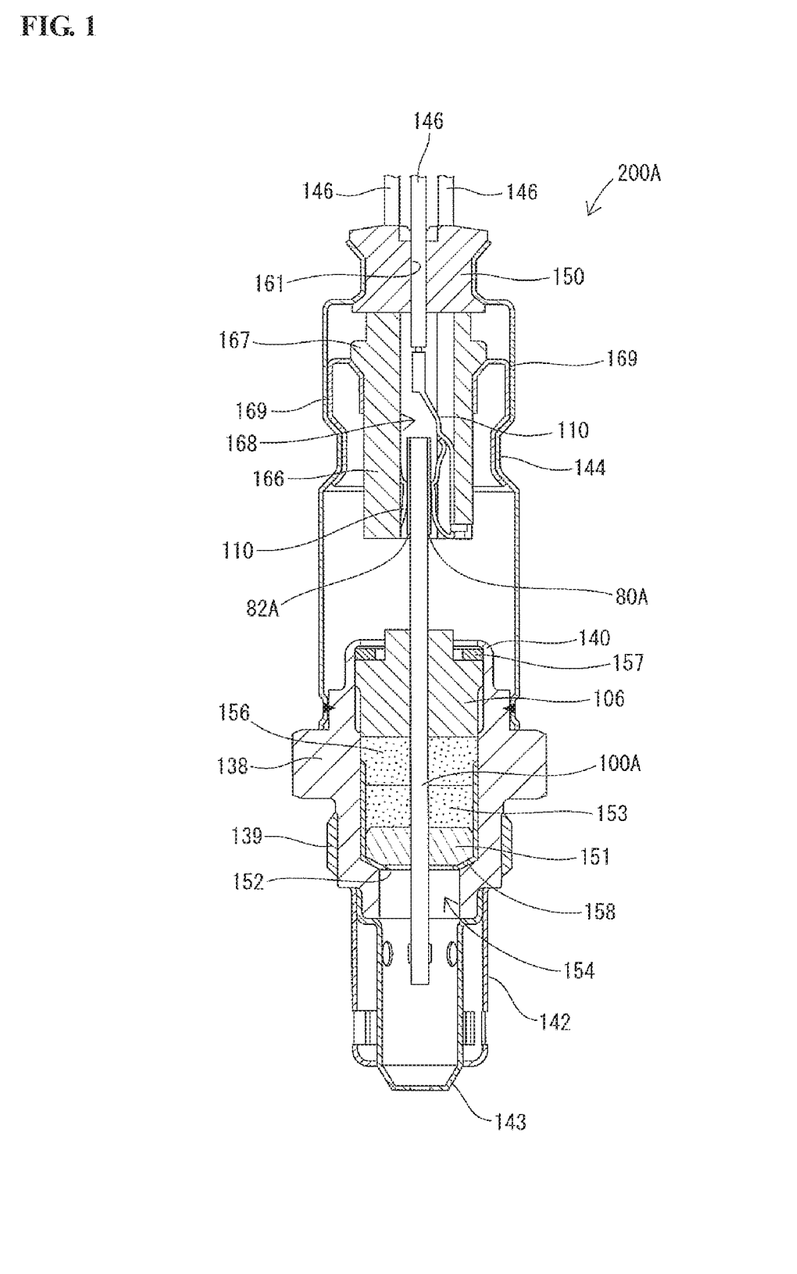
FIG. 1 is a longitudinal cross-sectional view of a multi-gas sensor according to one embodiment of the present invention.
Figure 2:
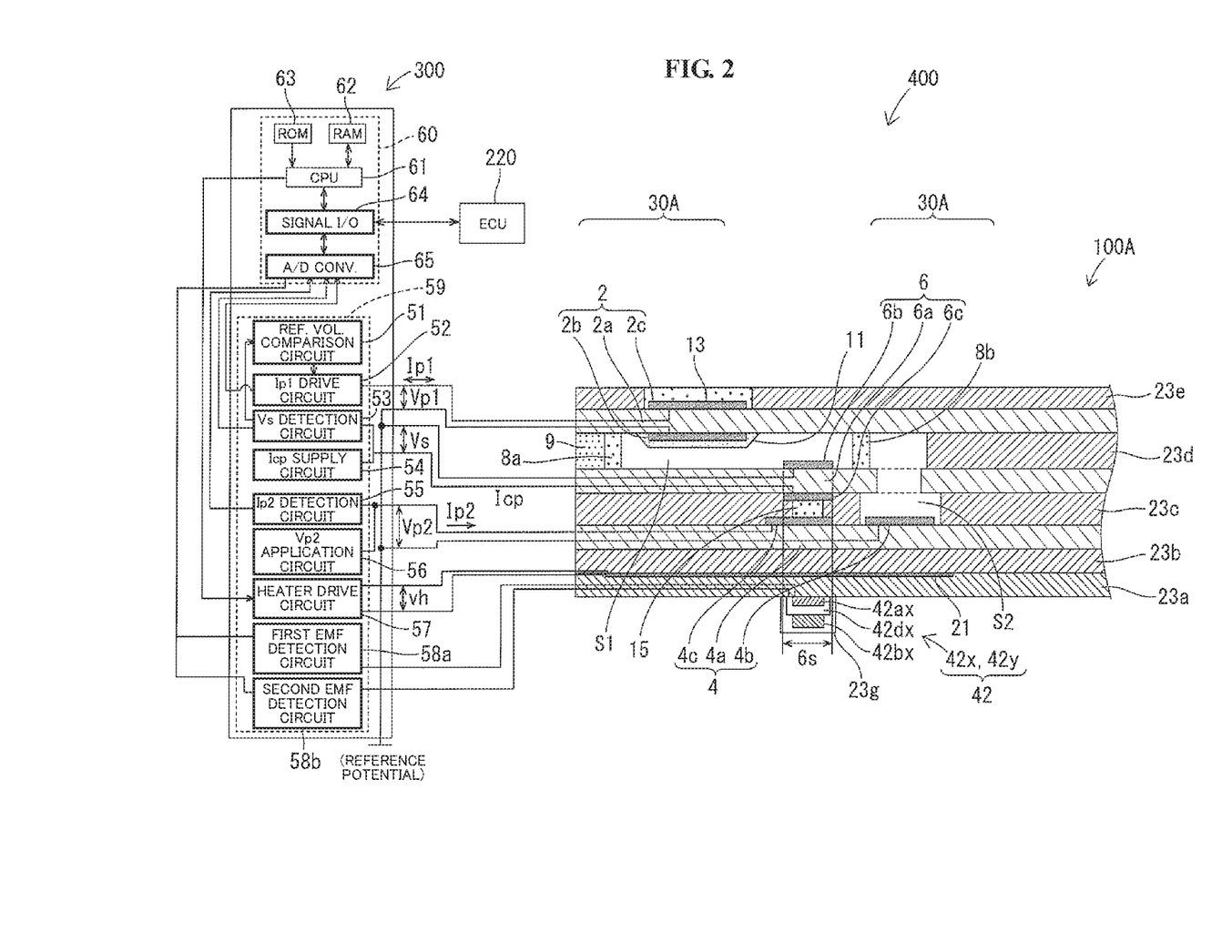
FIG. 2 is a block diagram of a multi-gas sensor apparatus with the multi-gas sensor of FIG. 1 and a sensor controller.

FIG. 1 is a longitudinal cross-sectional view of a multi-gas sensor 200A according to one embodiment of the present invention. FIG. 2 is a block diagram of a multi-gas sensor apparatus 400 equipped with the multi-gas sensor 200A and a sensor controller 300. In the present embodiment, the multi-gas sensor apparatus 400 is designed for use in a urea SCR system, which is for purifying nitrogen oxides (NOx) in an exhaust gas of an internal combustion engine of a vehicle by reaction of NOx with ammonia (urea), and is configured to measure the concentrations of nitrogen monoxide (NO), nitrogen dioxide ($NO_2$) and ammonia in the exhaust gas (as a gas under measurement) after the reaction of NOx and ammonia. There is no particular limitation on the engine to which the multi-gas sensor apparatus 400 is applied. The engine can be a diesel engine or a gasoline engine.

First, the basic configuration of the multi-gas sensor 200A and the system configuration of the multi-gas sensor apparatus 400 will be explained below.

As shown in FIG. 1, the multi-gas sensor 200A is in the form of an assembly including a multi-gas sensor unit 100A for detecting the concentrations of ammonia and NOx in the gas under measurement. The multi-gas sensor unit 100A has an elongated plate shape extending in an axial direction of the multi-gas sensor 200A. The multi-gas sensor 200A further includes: a substantially cylindrical metal shell 138 having formed on an outer circumferential surface thereof a thread portion 139 for fixing the multi-gas sensor 200A to an exhaust pipe of the engine; an annular ceramic sleeve 106 arranged radially around the multi-gas sensor unit 100A within the metal shell 138; a cylindrical insulating contact member 166 having a contact insertion hole 168 formed therethrough in the axial direction and arranged to surround a rear end portion of the multi-gas sensor unit 100A by an inner wall surface of the contact insertion hole 168; and a plurality of connection terminals 110 disposed between the multi-gas sensor unit 100A and the insulating contact member 166. In FIG. 1, only two connection terminals 110 are shown for simplification purposes.

The metal shell 138 has a substantially cylindrical shape, with a through hole 154 formed therethrough in the axial direction and a shelf portion 152 protruding radially inwardly in the through hole 154. The multi-gas sensor unit 100A is held in the though hole 154 of the metal shell 138 such that a front end portion of the multi-gas sensor unit 100A is exposed outside from a front end of the metal shell 138 and such that electrode terminals 80A and 82A on opposite main surfaces of the rear end portion of the multi-gas sensor unit 100A are exposed outside from a rear end of the metal shell 138. The shelf portion 152 defines an inward tapered surface inclined with respect to a plane perpendicular to the axial direction.

An annular ceramic holder 151, annular filled layers 153 and 156 of talc powder (hereinafter respectively referred to as "talc rings 153 and 156") and the annular ceramic sleeve 106 are arranged, in this order from the front side toward the rear side, on an outer circumference of the multi-gas sensor unit 100A. A crimp packing 157 is arranged between the ceramic sleeve 106 and a rear end portion 140 of the metal shell 138. The rear end portion 140 of the metal shell 138 is crimped to push the ceramic sleeve 106 toward the front side via the crimp packing 157. A metal holder 158 is arranged between the ceramic holder 151 and the shelf portion 152 of the metal shell 138 so as to hold the talc ring 153 and the ceramic holder 151 and maintain gas-tightness.

A double-structure protector with outer and inner protector members 142 and 143 is fixed by e.g. welding to a front end portion of the metal shell 138 so as to cover the protruding front end portion of the multi-gas sensor unit 100A. The outer and inner protector members 142 and 143 are each made of a metal material (such as stainless steel) and have formed therein a plurality of holes.

An outer tube 144 is fixed around the rear end portion of the metal shell 138. A grommet 150 is fitted in a rear end opening of the outer tube 144. A lead insertion hole 161 is formed through the grommet 150 in the axial direction such that a plurality of leads 146 are inserted in the lead insertion hole 161 and electrically connected to the electrode terminals 80A, 82A via the connection terminals 110. In FIG. 1, only three leads 146 are shown for simplification purposes. Although the electrode terminals of the multi-gas sensor unit 100A are typified by two electrode terminals 80A, 82A in FIG. 1 for simplification purposes, the multi-gas sensor unit 100A in practice has a plurality of electrode terminals corresponding to the number of electrodes of the after-mentioned sensor parts 30A and 42 of the multi-gas sensor unit 100A.

The insulating contact member 166 is arranged around the protruding rear end portion of the multi-gas sensor unit 100A so as to surround the electrode terminals 80A and 82A on the rear end portion of the multi-gas sensor unit 100A. The insulating contact member 166 is generally cylindrical-shaped, with a collar portion 167 protruding radially outwardly from an outer surface thereof, and is retained in the outer tube 144 by contact of the collar portion 167 with the outer tube 144 via a retaining member 169. The connection terminals 110 are held in the contact insertion hole 168 of the insulating contact member 166 and electrically connected to at front end sides thereof to the electrode terminals 80A and 82A of the multi-gas sensor unit 100A and at rear end sides thereof to the leads 146.

As shown in FIG. 2, the multi-gas sensor 200A (multi-gas sensor unit 100A) is connected to the sensor controller 300 by coupling terminal ends of the leads 146 to sensor connectors and connecting these sensor connectors to connectors of the sensor controller 300. (In FIG. 2, the multi-gas sensor unit 100A is shown in cross section for convenience of explanation.) The sensor controller 300 is placed on the vehicle to which the internal combustion engine and the multi-gas sensor apparatus 400 are mounted, and is electrically connected to an ECU 220 of the vehicle.

Next, the detailed configuration of the multi-gas sensor unit 100A will be explained below.

The multi-gas sensor unit 100A includes a NOx sensor part 30A and an ammonia sensor part 42 (as an ammonia sensor element) as shown in FIG. 2.

The NOx sensor part 30A is of the same structure as that of a known NOx sensor. More specifically, the NOx sensor part 30A has a structure in which an insulating layer 23e, a first solid electrolyte body 2a, an insulating layer 23d, a third solid electrolyte body 6a, an insulating layer 23c, a second solid electrolyte body 4a and insulating layers 23b and 23a are stacked together in this order. There is a first measurement chamber S1 defined between the first solid electrolyte body 2a and the third solid electrolyte body 6a. A first diffusion limiting member 8a is arranged at an inlet side of the first measurement chamber S1 such that the exhaust gas (as the gas under measurement) is introduced from the outside into the first measurement chamber S1 through the first diffusion limiting member 8a. A protection layer 9 is formed of a porous material on an outer side of the first diffusion limiting member 8a. A second diffusion limiting member 8b is arranged at an outlet side of the first measurement chamber S1 (opposite from the inlet side). There is a second measurement chamber S2 (as a NOx measurement chamber) defined between the first solid electrolyte body 2a and the second solid electrolyte body 4a through the third solid electrolyte body 6a at a position adjacent to the second diffusion limiting member 8b (i.e. on the right side of the second diffusion limiting member 8b in FIG. 2). The second measurement chamber S2 is in communication with the first measurement chamber S1 through the second diffusion limiting member 8b.

An elongated plate-shaped heating resistor 21 is embedded between the insulating layers 23b and 23a so as to extend in the axial (longitudinal) direction of the multi-gas sensor unit 100A. The heating resistor 21 has a heating portion located on a front end side thereof and a pair of lead portions extending from the heating portion toward the rear in the axial direction. The heating resistor 21 and the insulating layers 23b and 23a serve together as a heater section for heating the multi-gas sensor 200A to an activation temperature to enhance the oxygen ion conductivity of the solid electrolyte bodies 2a, 4a and 6a and stabilize operation of the multi-gas sensor 200A.

The insulating layers 23a, 23b, 23c, 23d and 23e are each predominantly made of alumina. The first and second diffusion limiting members 8a and 8b are each made of a porous material such as alumina. The heating resistor 21 is made of platinum etc. There is no particular limitation on the pattern of the heating portion of the heating resistor 21. For example, the heating portion of the heating resistor 21 can be formed into a meandering pattern.

The first solid electrolyte body 2a is predominantly made of oxygen-ion-conductive zirconia and is sandwiched between an inner first pumping electrode 2b and an outer first pumping electrode 2c (as a counter electrode). Herein, the first solid electrolyte body 2a and the first pumping electrodes 2b and 2c constitute a first pumping cell 2. The inner and outer first pumping electrodes 2b and 2c are each predominantly made of platinum. The inner first pumping electrode 2b is arranged facing and exposed to the first measurement chamber S1. A surface of the inner first pumping electrode 2b is covered with a protection layer 11 of porous material. The outer first pumping electrode 2c is arranged in a hollow portion of the insulating layer 23e and opposed to the inner first pumping electrode 2b via the solid electrolyte layer 2a. This hollow portion is filled with a porous material 13 so as to allow a flow of gas (oxygen) between the outer first pumping electrode 2c and the outside.

The third solid electrolyte body 6a is predominantly made of zirconia and is sandwiched between a detection electrode 6b and a reference electrode 6c. Herein, the third solid electrolyte body 6a, the detection electrode 6b and the reference electrode 6c constitute an oxygen concentration detection cell 6. The detection electrode 6b and the reference electrode 6c are each predominantly made of platinum. The detection electrode 6b is arranged facing and exposed to the first measurement chamber S1 at a position downstream of the inner first pumping electrode 2b. The reference electrode 6c is arranged in a hollow portion of the insulating layer 23c. This hollow portion is filled with a porous material, thereby defining a reference oxygen chamber 15. With the supply of a predetermined small current Icp from the after-mentioned Icp supply circuit 54 to the oxygen concentration detection cell 6, oxygen is pumped from the first measurement chamber S1 into the reference oxygen chamber 15 as reference oxygen.

The second solid electrolyte body 4a is predominantly made of zirconia. An inner second pumping electrode 4b and a second pumping counter electrode 4c are disposed on a second measurement chamber S2-side surface of the second solid electrolyte body 4a. Herein, the second solid electrolyte body 4a, the inner second pumping electrode 4b and the second pumping counter electrode 4c constitute a second pumping cell 4a. The inner second pumping electrode 4b and the second pumping counter electrode 4c are each predominantly made of platinum. The second pumping electrode 4b is arranged facing and exposed to the second measurement chamber S2. The second pumping counter electrode 4c is arranged in a hollow portion of the insulating layer 23c at a position opposed to the reference electrode 6c and facing the reference oxygen chamber 15.

The inner first pumping electrode 2b, the detection electrode 6b and the inner second pumping electrode 4b are each connected to a reference potential. In the present embodiment, a portion of the NOx sensor part 30A except the heating resistor 21 and the insulating layers 23b and 23a (more specifically, the first pumping cell 2, the oxygen concentration detection cell 6 and the second pumping cell 4) serves as a NOx detection section.

On the other hand, the ammonia sensor part 42 includes two (first and second) mixed potential type ammonia detection cells 42x and 42y.

Figure 3:
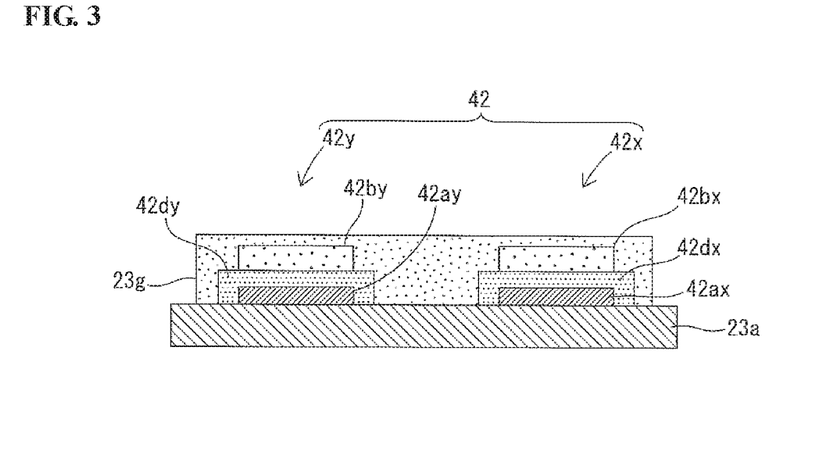
FIG. 3 is a cross-sectional view of first and second ammonia detection cells of the multi-gas sensor of FIG. 1.

FIG. 3 is a cross-sectional view of the ammonia sensor part 42. As shown in FIG. 3, the first and second ammonia detection cells 42x and 42y are located apart from each other in a width direction of the multi-gas sensor element 100A (perpendicular to the axial direction) and are disposed on an outer surface of the insulating layer 23a (i.e. on an outer surface of the NOx sensor part 30A).

The first ammonia detection cell 42x has a first reference electrode 42ax arranged on the insulating layer 23a, a first solid electrolyte body 42dx arranged to cover outer and side surfaces of the first reference electrode 42ax and a first detection electrode 42bx (as a first ammonia detection electrode) arranged on an outer surface of the first solid electrolyte body 42x (opposite from the first reference electrode 42ax) so as to detect the concentration of ammonia in the gas under measurement according to a change in electromotive force between the first reference electrode 42ax and the first detection electrode 42bx.

Similarly, the second ammonia detection cell 42y has a second reference electrode 42ay arranged on the insulating layer 23a, a second solid electrolyte body 42dy arranged to cover outer and side surfaces of the second reference electrode 42ay and a second detection electrode 42by (as a second ammonia detection electrode) arranged on an outer surface of the second solid electrolyte body 42dy (opposite from the second reference electrode 42ay) so as to detect the concentration of ammonia in the gas under measurement according to a change in electromotive force between the second reference electrode 42ay and the second detection electrode 42by.

In the present embodiment, the first and second ammonia detection cells 42x and 42y are stacked on the NOx detection section, with the heater section (i.e. the heating resistor 21 and the insulating layers 23b and 23a) interposed between the NOx detection section and the ammonia detection cells 42x and 42y in the stacking direction, as mentioned above. Namely, both of the NOx detection section and the ammonia detection cells 42x and 42y are located adjacent to (at substantially the same distance from) the heater section. The control temperature of the oxygen concentration detection cell 6 in the NOx sensor part 30A is thus more accurately reflected in the control of the ammonia detection cells 42x and 42y in the present embodiment as compared to the case where the NOx detection section and the ammonia detection cells are located on one side of the heater section in the stacking direction. This allows more accurate temperature control of the ammonia detection cells 42x and 42y.

Furthermore, each of the first and second ammonia detection cells 42x and 42y has a pair of electrodes 42ax and 42bx or 42ay and 42by arranged on opposite surfaces of the solid electrolyte body 42dx, 42dy in the present embodiment. Among the respective electrode pairs, the first reference electrode 42ax and the second reference electrode 42ay are disposed on the outer surface of the NOx sensor part 30A. In such arrangement, the plane dimensions of the solid electrolyte bodies 42dx and 42dy can be decreased as compared to the case where each pair of electrodes is disposed on one surface of the solid electrode body 42dx, 42dy. Consequently, the dimensions of the first and second ammonia detection cells 42x and 42y can be decreased so as to allow a size reduction of the ammonia detection cells 42x and 42y. This makes it easier to achieve the following arrangement structure of a protection layer 23 on the ammonia detection cells 42x and 42y and, at the same time, makes it possible to reduce the occurrence of a temperature distribution depending on the positions of the ammonia detection cells 42x and 42y and thereby reduce the temperature dependence of the $NO_x/NH_3$ sensitivity ratio between the first and second ammonia detection cells 42x and 42y so that the multi-gas sensor apparatus 400 enables more accurate detection of the NOx and ammonia concentrations. In the case where the size reduction of the ammonia detection cells 42x and 42y is not particularly required, each of the ammonia detection cells 42x and 42y may have a pair of electrodes on one surface of the solid electrolyte body 42dx, 42dy.

As shown in FIG. 3, the protection layer 23g is formed of a porous material so as to integrally cover both of the first and second ammonia detection cells 42x and 42y. This protection layer 23g performs the functions of not only preventing adhesion of poisoning substance to the first and second detection electrodes 42bx and 42by but also adjusting the rate of diffusion of the gas under measurement from the outside into the first and second ammonia detection cells 42x and 42y. The porous material of the protection layer 23g can be at least one kind of material selected from the group consisting of alumina (aluminum oxide), spinel ($MgAl_2O_4$), silica alumina and mullite. The rate of diffusion of the gas under measurement through the protection layer 23g can be adjusted by varying the thickness, particle size, particle distribution, porosity, material mixing ratio etc. of the protection layer 23g.

As the protection layer 23g is formed to integrally cover both of the first and second ammonia detection cells 42x and 42y as shown in FIG. 3, the protection layer 23g is uniform in porosity (gas permeability) at positions corresponding to the first and second ammonia detection cells 42x and 42y. The gas under measurement can be thus introduced at the same rate into the first and second ammonia detection cells 42x and 42y through the protection layer 23g. This makes it possible to prevent or reduce a change of the sensitivity ratio between the first and second ammonia detection cells 42x and 42y caused by the protection layer 23g so that the multi-gas sensor apparatus 400 enables more accurate detection of the NOx and ammonia concentrations.

Although the ammonia detection cells 42x and 42y are integrally covered by the protection layer 23 in the present embodiment, the configuration of the multi-gas sensor unit 100A is not limited to this embodiment. Alternatively, the ammonia detection cells 42x and 42y may be exposed to the outside without being covered by the protection layer 23. As another alternative, separate protection layers may be respectively formed on the first and second ammonia detection cells 42x and 42y so as to adjust the sensitivity ratio between the first and second ammonia detection cells 42x and 42y.

The first and second detection electrodes 42bx and 42by are each formed of a material containing Au as a predominant component (e.g. in an amount of 70 mass % or more); whereas the first and second reference electrodes 42ax and 42ay are each formed of Pt solely or a material containing Pt as a predominant component (e.g. in an amount of 70 mass % or more). Since Au is low in catalytic activity, ammonia gas is difficult to burn at a surface of the Au-predominant detection electrode 42bx, 42by. When ammonia gas passes through the detection electrode 42bx, 42by, electrode reaction of ammonia with oxygen ions takes place at the interface between the detection electrode 42bx, 42by and the reference electrode 42ax, 42ay. As a result of the electrode reaction, there develops a change in electromotive force between the detection electrode 42bx, 42by and the reference electrode 42ax, 42ay in accordance with the concentration of ammonia gas. In the present embodiment, the first and second detection electrodes 42bx and 42by have different $NO_x/NH_3$ sensitivity ratios due to different metal compositions. The first and second solid electrolyte bodies 42dx and 42dy are each formed of e.g. yttria stabilized zirconia (YSZ).

In the present embodiment, the multi-gas sensor apparatus 400 is configured to measure the impedance of the oxygen concentration detection cell 6 and control heating operation of the heater section (heating resistor 21) based on the measured impedance. In this configuration, the temperature of the multi-gas sensor unit 100A in the vicinity of the oxygen concentration detection cell 6 is maintained at the most stable (temperature-identifiable) value. The greater the distance from the oxygen concentration cell 6 in the axial direction, the larger the change in temperature of the multi-gas sensor unit 100A caused under the influence of the outside temperature.

Each of the first and second ammonia detection cells 42x and 42y is hence situated to at least partially overlap a first region 6s of the oxygen concentration detection cell 6, such that the temperatures of the first and second ammonia detection cells 42x and 42y are maintained constant within a predetermined range for improvement of ammonia detection accuracy.

Figure 4:
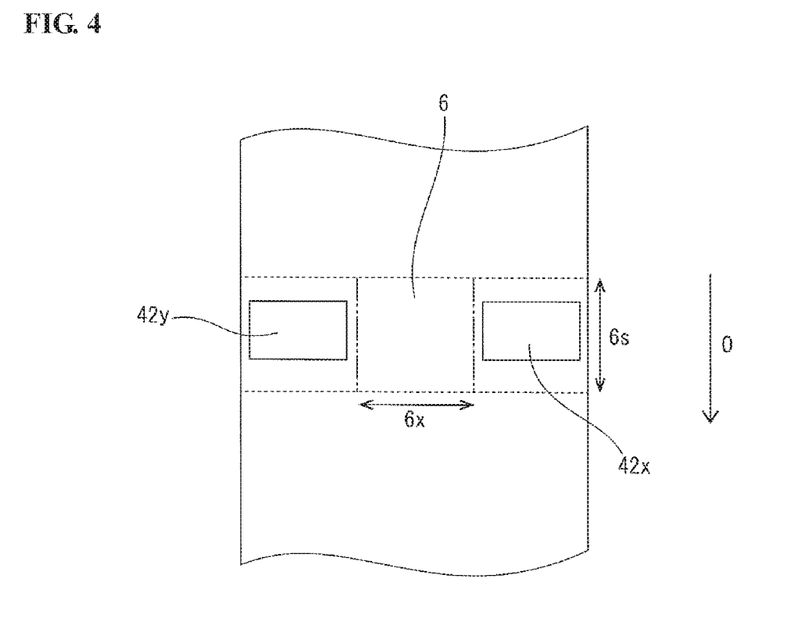
FIG. 4 is a plan view showing a positional relationship between the first and second ammonia detection cells and an oxygen concentration detection cell of the multi-gas sensor of FIG. 1.

FIG. 4 is a plan view showing the positional relationship of the first and second ammonia detection cells 42x and 42y and the oxygen concentration detection cell 6. In FIG. 4, the axial (longitudinal) direction of the multi-gas sensor unit 100A is indicated by an arrow O. As indicated by dotted lines in FIG. 4, the first region 6s is defined by both ends of the oxygen concentration detection cell 6 in the axial direction O (also see FIG. 2). Further, a second region 6x of the oxygen concentration detection cell 6 is defined as a part of the first region 6s ranging between both ends of the oxygen concentration detection cell 6 in the width direction as indicated by two-dot chain lines in FIG. 4.

Since the detection electrode 6b and the reference electrode 6c are of the same dimension and are at the same position in the axial (longitudinal) direction of the multi-gas sensor unit 100A in the present embodiment, the first region 6s is defined by the front and rear ends of the electrodes 6b and 6c in the axial direction O; and the second region 6x is defined by both ends of the electrodes 6b and 6c in the width direction.

In the case where the detection and reference electrodes 6b and 6c are of different dimensions or in the case where the detection and reference electrodes 6b and 6c are displaced in position, the axial-direction ends (front and rear ends) and width-direction ends of the area in which both the electrodes 6b and 6c are present as viewed in the stacking direction are used as the references for the positions of the first and second regions 6s and 6x. Namely, frontward and rearmost ones of the ends of the electrodes 6b and 6c in the axial direction are used as the references for the position of the first region 6s; and outermost ones of the ends of the electrodes 6b and 6c in the width direction are used as the reference for the position of the second region 6x.

The same applies to the position of the ammonia detection cell 42x (42y). In the case where the detection electrode 42bx (42by) and the reference electrode 42ax (42ay) are positioned on both surfaces of the solid electrolyte body 42dx (42dy), the axial-direction ends (front and rear ends) and width-direction ends of the area in which both the electrodes 42ax and 42bx (42ay and 42by) are present as viewed in the stacking direction are used as the references for the position of the ammonia detection cell 42x (42y). Even in the case where the detection electrode 42bx (42by) and the reference electrode 42ax (42ay) are positioned on one surface of the solid electrolyte body 42dx (42dy), the axial-direction ends and width-direction ends of the area in which both the electrodes 42ax and 42bx (42ay and 42by) are present are used as the references for the position of the ammonia detection cell 42x (42y).

More specifically, each of the first and second ammonia detection cells 42x and 42y are situated to entirely overlap the first region 6s in the axial direction as shown in FIGS. 2 and 4 in the present embodiment. In other words, the first and second ammonia detection cells 42x and 42y entirely overlap and correspond in position to each other in the axial direction within the first region 6s. Moreover, the oxygen concentration detection cell 6 is situated at the center of the multi-gas sensor unit 100A in the width direction; and the first and second ammonia detection cells 42x and 42y are situated on opposite sides of the second region 6x in the width direction so as to sandwich therebetween the oxygen concentration detection cell 6.

As explained above, the first and second ammonia detection cells 42x and 42y are situated within the first region 6s on the outer surface of the NOx sensor part 30A so as to at least partially overlap each other in the present embodiment. Since the temperature control of the multi-gas sensor unit 100A is performed with reference to the oxygen concentration detection cell 6, the temperature of the multi-gas sensor unit 100A in the vicinity of the oxygen concentration detection cell 6 is reliably maintained at the most stable (temperature-identifiable) value. The temperatures of the first and second ammonia detection cells 42x and 42y, which are situated within the first region 6s in the vicinity of the oxygen concentration detection cell 6, are also maintained at stable values. This makes it possible to reduce the temperature dependence of the sensitivity ratio.

As the first and second ammonia detection cells 42x and 42y entirely overlap the first region 6s in the present embodiment, the entire first and second ammonia detection cells 42x and 42y are reliably located close to the oxygen concentration detection cell 6. This makes it possible to further reduce the temperature dependence of the sensitivity ratio.

Further, both of the first and second ammonia sensor parts 42x and 42y are located adjacent to the oxygen concentration detection cell 6 as the first and second ammonia detection cells 42x and 42y are arranged on opposite sides of the second region 6x in the width direction. The temperature difference between the first and second ammonia sensor parts 42x and 42y can be thus suppressed as compared to the case where either one of the first and second ammonia detection cells 42x and 42y is located adjacent to the oxygen concentration detection cell 6 by the arrangement of the first and second ammonia sensor parts 42x and 42y on one side of the oxygen concentration detection cell 6 in the width direction. This also makes it possible to further reduce the temperature dependence of the sensitivity ratio.

Furthermore, the first and second ammonia detection cells 42x and 42y are located at substantially the same distance apart from the second region 6x in the width direction. This also makes it possible to suppress the temperature difference between the first and second ammonia detection cells 42x and 42y and thereby further reduce the temperature dependence of the sensitivity ratio.

The heater section (more specifically, the heating resistor 21) causes a heat distribution in the axial direction due to the axial arrangement of the heating portion and the lead portions. In the present embodiment, however, the first and second ammonia detection cells 42x and 42y at least partially overlap each other in the axial diction so that the overlap parts of the first and second ammonia sensor parts 42x and 42y are axially uniformly subjected to heat from the heater section. The first and second ammonia sensor parts 42x and 42y are more uniformly subjected to heat from the heater section when the first and second ammonia detection cells 42x and 42y entirely overlap and correspond in position to each other in the axial direction as in the present embodiment. This also makes it possible to further reduce the temperature dependence of the sensitivity ratio.

In the present embodiment, the lengths of the first and second ammonia detection cells 42x and 42y in the axial direction are set smaller than the length of the first region 6s in the axial direction so that both of the first and second ammonia detection cells 42x and 42y are situated within the first region 6s in the axial direction. With such small axial dimensions of the first and second ammonia detection cells 42x and 42y, the multi-gas sensor element 100A can be reduced in size while suppressing the temperature distribution of the ammonia detection cells 42x and 42y in the axial direction to reduce the temperature dependence of the sensitivity ratio.

The configuration of the sensor controller 300 will be next explained below.

Referring back to FIG. 2, the sensor controller 300 has a control circuit (analog control circuit) module 59 and a microcomputer 60 both mounted on a circuit board.

The microcomputer 60 is configured to control the whole of the gas sensor controller 300. As shown in FIG. 2, the microcomputer 60 is provided with a CPU (central processing unit) 61, a RAM 62, a ROM 63, a signal input/output part 64, a A/D converter 65, a clock (not shown) and the like such that various programs stored in the ROM 63 etc. are executed by the CPU 61.

The control circuit module 59 is configured to control operation of the multi-gas sensor 200A and output detection values of the multi-gas sensor 200A to the microcomputer 60. As shown in FIG. 2, the control circuit module 59 is provided with a reference voltage comparison circuit 51, a IP1 drive circuit 52, a Vs detection circuit 53, a Icp supply circuit 54, a Ip2 detection circuit 55, a Vp2 application circuit 56, a heater drive circuit 57 and first and second electromotive force detection circuits 58a and 58b.

The first electromotive force detection circuit 58a is connected to the electrodes 42ax and 42bx of the first ammonia detection cell 42x, whereas the second electromotive force detection circuit 58b is connected to the electrodes 42ay and 42by of the second ammonia detection cell 42y.

The first electromotive force detection circuit 58a detects an electromotive force (EMF) between the electrodes 42ax and 42bx of the first ammonia detection cell 42x as a first ammonia concentration output value and outputs the detected ammonia electromotive force to the microcomputer 60. The second electromotive force detection circuit 58b detects an electromotive force (EMF) between the electrodes 42ay and 42by of the second ammonia detection cell 42y as a second ammonia concentration output value and outputs the detected ammonia electromotive force to the microcomputer 60.

Further, the Ip1 drive circuit 52 is connected to the outer first pumping electrode 2c of the NOx sensor part 30A. The Vs detection circuit 53 and the Icp supply circuit 54 are connected in parallel to the reference electrode 6c of the NOx sensor part 30A. The Ip detection circuit 55 and the Vp2 application circuit 56 are connected in parallel to the second pumping counter electrode 4c of the NOx sensor part 30A. Further, the heater drive circuit 57 is connected to the heater section (heating resistor 21) of the NOx sensor part 30A.

The Ip1 drive circuit 52 supplies a first pumping current Ip1 between the inner and outer first pumping electrodes 2b and 2c while detecting and controlling the first pumping current Ip1. Further, the Ip1 drive circuit 52 outputs the detected first pumping current Ip1 to the A/D converter 65.

The Vs detection circuit 53 detects a voltage Vs between the detection electrode 6b and the reference electrode 6c and outputs the detected voltage Vs to the reference voltage comparison circuit 51. The reference voltage comparison circuit 51 compares the output (voltage Vs) of the Vs detection circuit 53 with a reference voltage (e.g. 425 mV) and outputs the comparison result to the Ip1 drive circuit 52. Based on the comparison result, the direction and magnitude of the first pumping current Ip1 are controlled by the Ip1 drive circuit 52 so as to set the voltage Vs equal to the reference voltage and thereby adjust the concentration of oxygen in the first measurement chamber S1 to a predetermined level at which the decomposition of NOx does not occur.

The Icp supply circuit 54 supplies a small current Icp between the detection electrode 6b and the reference electrode 6c. By the supply of the current Icp, oxygen is pumped from the first measurement chamber S1 to the reference oxygen chamber 15 so that the reference electrode 6c is exposed to a predetermined reference oxygen concentration.

The Vp2 application circuit 56 applies, between the inner second pumping electrode 4b and the second pumping counter electrode 4c, a constant voltage Vp2 (e.g. 450 mV higher than the control voltage of the oxygen concentration detection cell 6) at which NOx in the gas under measurement is decomposed into oxygen gas and $N_2$ gas.

The Ip2 detection circuit 55 detects a second pumping current Ip2 flowing in the second pumping cell 4 at the time when oxygen generated by decomposition of NOx is pumped from the second measurement chamber S2 to the second pumping counter electrode 4c side through the second solid electrolyte body 4a. Further, the Ip2 detection circuit 55 outputs the detected second pumping current Ip2 to the A/D converter 65. Upon receipt of the pumping currents Ip1 and Ip2 from the Ip drive circuit 52 and the Ip2 detection circuit 55, the A/D converter 65 converts these current values into digital signals and outputs the digital signals to the CPU 61 via the signal input/output part 64.

The heater drive circuit 57 performs drive control of the heater section (heating resistor 21).

One example of control process executed by the control circuit module 59 of the sensor controller 300 will be explained below.

When the engine is started, the control circuit module 59 is supplied with power from an external power source. Then, the heater drive circuit 59 drives the heater section to heat the NOx sensor part 30A (i.e. the first pumping cell 2, the oxygen concentration detection cell 6 and the second pumping cell 4) to an activation temperature. Further, the Icp supply circuit 54 supplies a small current Icp between the detection electrode 6b and the reference electrode 6e of the oxygen concentration detection cell 6 so as to pump oxygen from the first measurement chamber S1 to the reference oxygen chamber 15 and set a predetermined reference oxygen concentration in the reference oxygen chamber 15. As the NOx sensor part 30A becomes heated to an adequate temperature by the heater section, the temperatures of the first and second ammonia detection cells 42x and 42y on the NOx sensor part 30A are increased with increasing temperature of the NOx sensor part 30A.

When the respective sensor cells are heated to the activation temperature, the Ip1 drive circuit 51 supplies a first pumping current Ip1 between the electrodes 2b and 2c of the first pumping cell 2 so that the first pumping cell 2 pumps oxygen in the gas under measurement in the first measurement chamber S1 from the inner first pumping electrode 2b to the outer first pumping electrode 2c. At this time, the concentration of oxygen in the first measurement chamber S1 is set corresponding to the voltage Vs between the electrodes 6b and 6c of the oxygen concentration detection cell 6. The direction and magnitude of the first pumping current Ip1 are accordingly controlled so as to set the interelectrode voltage Vs equal to the reference voltage and thereby adjust the concentration of oxygen in the first measurement chamber S1 to a predetermined level at which the decomposition of NOx does not occur.

The gas under measurement whose oxygen concentration has been adjusted as above is fed into the second measurement chamber S2. The Vp2 application circuit 56 applies between the electrodes 4b and 4c of the second pumping cell 4 a constant voltage Vp2 (e.g. 450 mV) at which NOx in the gas under measurement is decomposed into oxygen gas and $N_2$ gas. Then, a second pumping current Ip2 flows in the second pumping cell 4 so as to pump the thus-generated oxygen gas into the second measurement chamber S2. The Ip2 detection circuit 55 detects the second pumping cell Ip2. Since the second pumping current Ip2 is proportional to the concentration of NOx, the concentration of NOx in the gas under measurement is determined based on the second pumping current Ip2.

On the other hand, the first electromotive force detection circuit 58a detects an electromotive force between the pair of electrodes 42ax and 42bx as an ammonia concentration output value; and the second electromotive force detection circuit 58b detects an electromotive force between the pair of electrodes 42ay and 42by as an ammonia concentration output value. As will be explained below, the concentration of ammonia in the gas under measurement is determined based on these ammonia concentration output values.

Various gas concentration determination processes executed by the microcomputer 60 of the sensor controller 300 will be next explained below.

In the present embodiment, the ammonia sensor part 42 is provided with two ammonia detection cells 42x and 42y in view of the facts that: the ammonia detection cell detects not only $NH_3$ gas but also $NO_2$ gas; and hence, when $NO_2$ gas is contained together with $NH_3$ in the gas under measurement, the $NH_3$ concentration detection accuracy of the ammonia detection cell is deteriorated. When two ammonia detection cells 42x and 42y of different $NOx/NH_3$ sensitivity ratios are provided as in the present embodiment, detection values are respectively outputted from two ammonia detection cells 42x and 42y at different sensitivities against two unknown concentrations of $NH_3$ gas and $NO_2$ gas in the present embodiment. The concentrations of $NH_3$ and $NO_2$ in the gas under measurement are determined using these output values.

The term "$NOx/NH_3$ sensitivity ratio" as used herein refers to the ratio of the sensitivity of detection of $NH_3$ to the overall detection sensitivity (i.e. the sensitivity of detection of $NH_3$ and NOx) of the ammonia detection cell 42x, 42y. In the present embodiment, the ammonia detection cell 42x, 42y detects $NO_2$ gas but does not detect NO gas. Accordingly, the $NOx/NH_3$ sensitivity ratio of the ammonia detection cell 42x, 42y is regarded as the $NO_2/NH_3$ sensitivity ratio of the ammonia detection cell 42x, 42y. In the case where the ammonia detection cell 42x, 42y detects NO gas but does not detect $NO_2$ gas, the $NOx/NH_3$ sensitivity ratio of the ammonia detection cell 42x, 42y can be regarded as the $NO/NH_3$ sensitivity ratio of the ammonia detection cell 42x, 42y.

More specifically, the output value of the ammonia detection cell is expressed as a function F(x, y, D) where x is the $NH_3$ concentration; y is the $NO_2$ concentration; and D is the $O_2$ concentration. When two ammonia detection cells 42x and 42y of different sensitivity ratios are used, two functions $F_1$(mx, ny, D) and $F_2$(sx, ty, D) (where in, n, s and t are factors) are respectively obtained from the ammonia detection cells 42x and 42y. Since $F_1$, $F_2$ and D are read as the sensor outputs, two functions with two unknowns (x, y) are solved to remove y from these two functions and determine x according to the after-mentioned formulas (1) to (3).

The sensitivity ratios of the first and second ammonia detection cells 42x and 42y also change depending on the temperatures of the first and second ammonia detection cells 42x and 42y. In the present embodiment, however, the first and second ammonia detection cells 42x and 42y are situated to overlap at least a part of the first region 6s of the oxygen concentration detection cell 6 in the axial direction as mentioned above. The temperatures of the first and second ammonia detection cells 42x and 42y are thus maintained constant within a predetermined range so that the change of the sensitivity ratios of the ammonia detection cells 42x and 42y due to temperature difference can be reduced.

The detection of $NH_3$ and $NO_2$ by the first and second ammonia detection cells 42x and 42y and the determination of the $NH_3$ and $NO_2$ concentrations will be explained in more detail below.

There develops an electromotive force between the first reference electrode 42ax and the first detection electrode 42*bx* of the first ammonia detection cell 42*x* in accordance with the concentration of $NH_3$ in the gas under measurement. As mentioned above, the first electromotive force detection circuit 58*a* detects the electromotive force between the first reference electrode 42*ax* and the first detection electrode 42*bx* as a first ammonia electromotive force. Similarly, there develops an electromotive force between the second reference electrode 42*ay* and the second detection electrode 42*by* of the second ammonia detection cell 42*y* in accordance with the concentration of $NH_3$ in the gas under measurement. The second electromotive force detection circuit 58*b* also detects the electromotive force between the second reference electrode 42*ay* and the second detection electrode 42*by* as a second ammonia electromotive force as mentioned above.

The CPU 61 of the microcomputer 60 retrieves various data stored in the ROM 63 upon receipt of the output values (first and second pumping currents Ip1 and Ip2 and first and second ammonia electromotive forces) from the respective sensor cells 2, 4, 42*x* and 42*y*, and then, and executes processing operations on these cell output values according to the retrieved data.

The data stored in the ROM 63 includes, for example, a "first ammonia electromotive force-first ammonia concentration output relational equation", "second ammonia electromotive force-second ammonia concentration output relational equation", "first pumping current Ip1-$O_2$ concentration output relational equation", "second pumping current Ip2-NOx concentration output relational equation", "first and second ammonia concentration output and $O_2$ concentration output-corrected ammonia concentration output relational equation" (as correction formula (1); see below), "first and second ammonia concentration output and $O_2$ concentration output-corrected $NO_2$ concentration output relational equation" (as correction formula (2); see below) and "NOx concentration output and corrected ammonia and corrected $NO_2$ concentration output-corrected NOx concentration output relational equation" (as correction formula (3); see below).

Although various data items are stored as relational equations in the ROM 63 as mentioned above in the present embodiment, the data items stored in the ROM can be in any other form such as tables that determine various gas concentrations from sensor outputs. The data items may be values (relational equations, tables) obtained using model gases of known gas concentrations.

The "first ammonia electromotive force-first ammonia concentration output relational equation" represents a relationship between the first ammonia electromotive force outputted from the first ammonia detection cell 42*x* and the $NH_3$ concentration of the gas under measurement. The "second ammonia electromotive force-second ammonia concentration output relational equation" represents a relationship between the second ammonia electromotive force outputted from the second ammonia detection cell 42*y* and the $NH_3$ concentration of the gas under measurement.

The "first pumping current Ip1-$O_2$ concentration output relational equation" represents a relationship between the first pumping current Ip1 and the $O_2$ concertation of the gas under measurement.

The "second pumping current Ip2-NOx concentration output relational equation" represents a relationship between the second pumping current Ip2 and the NOx concertation of the gas under measurement.

The "first and second ammonia concentration output and $O_2$ concentration output-corrected ammonia concentration output relational equation" represents a relationship between the first and second ammonia concentration output values under the influence of the $O_2$ and $NO_2$ concentrations and the corrected ammonia concentration value obtained by the removal of the influence of the $O_2$ and $NO_2$ concentrations.

The "first and second ammonia concentration output and $O_2$ concentration output-corrected $NO_2$ concentration output relational equation" represents a relationship between the $NO_2$ concentration output value under the influence of the $O_2$ and $NH_3$ concentrations and the corrected $NO_2$ concentration output value obtained by the removal of the influence of the $O_2$ and $NH_3$ concentrations.

The "NOx concentration output and corrected ammonia and $NO_2$ concentration output-corrected NOx concentration output relational equation" represents a relationship between the NOx concentration output value under the influence of the $NH_3$ and $NO_2$ concentrations and the accurate corrected NOx concentration output value obtained by the removal or correction of the influence of the $NH_3$ and $NO_2$ concentrations.

The conversion from the first pumping current Ip1, the second pumping current Ip2, the first ammonia electromotive force and the second ammonia electromotive force into the NOx concentration and the ammonia concentration by the CPU 61 of the microcomputer 60 will be explained in more detail below.

The CPU 61 converts the first pumping current Ip1 into a $O_2$ concentration value by referring to the "first pumping current Ip1-$O_2$ concentration output relational equation", and converts the second pumping current Ip2 into a NOx concentration value by referring to the "second pumping current Ip2-NOx concentration output relational equation".

Further, the CPU 61 converts the first and second ammonia electromotive forces into first and second ammonia concentration values by referring to the "first ammonia electromotive force-first ammonia concentration output relational equation" and the "second ammonia electromotive force-second ammonia concentration output relational equation". Herein, each of the "first ammonia electromotive force-first ammonia concentration output relational equation" and the "second ammonia electromotive force-second ammonia concentration output relational equation" is set such that the ammonia concentration output of the ammonia detection cell 42*x*, 42*y* is generally linearly proportional to the ammonia concentration of the gas under measurement within the entire range of electromotive force outputtable from the ammonia detection cell 42*x*, 42*y* under usage environment. The conversions according to these conversion equations enable calculations with changes of slope and offset in the following correction formulas.

The CPU 61 then determines the ammonia and NOx concentrations of the gas under measurement by substituting the above-obtained $O_2$ concentration value, NOx concentration value and first and second ammonia concentration values into the correction formulas (1), (2) and (3):

$$x=F(A,B,D)=(eA-c)\times(jB-h-fA+d)/(eA-c-iB+g)+fA-d \quad (1)$$

$$y=F''(A,B,D)=(jB-h-fA+d)/(eA-c-iB+g) \quad (2)$$

$$z=C-ax+by \quad (3)$$

where x is the ammonia concentration; y is the $NO_2$ concentration; z is the NOx concentration; A is the first ammonia concentration value; B is the second ammonia concentration value; C is the NOx concentration value; D is the $O_2$ concentration value; a and b are correction factors; and c, d, e, f, g, h, i and j are factors calculated using the $O_2$ concentration value D. In the correction formulas (1) and (2), F and F' mean that x is a function of A, B and D.

The correction formulas (1) and (2) are defined on the basis of the characteristics of the first and second ammonia detection cells 42x and 42y. The correction formula (3) is defined on the basis of the characteristics of the NOx sensor part 30A. These correction formulas (1), (2) and (3) are mere examples. It is feasible to utilize other correction formulas and factors depending on the gas detection characteristics of the sensor unit 100A.

The details of the first sensing electrode 42bx and the second sensing electrode 42by will be explained below.

As mentioned above, the multi-gas sensor unit 100A of the present embodiment is characterized in that the first detection electrode 42bx has a metal composition containing Au as a predominant component (e.g. in an amount of 70 mass % or more); and the second detection electrode 42by has a metal composition containing Au as a predominant component (e.g. in an amount of 70 mass % or more).

It is preferable that the metal composition of the first detection electrode 42bx further contains a metal having a higher melting point than that of Au and capable of alloying with Au. Although there is no particular limitation on the alloying metal, Pt is preferred as the alloying metal in the first detection electrode 42bx.

It is also preferable that the metal composition of the second detection electrode 42by further contains a metal having a higher melting point than that of Au and capable of alloying with Au. Although there is no particular limitation on the alloying metal, Pd is preferred as the alloying metal in the second detection electrode 42by.

Figure 5:
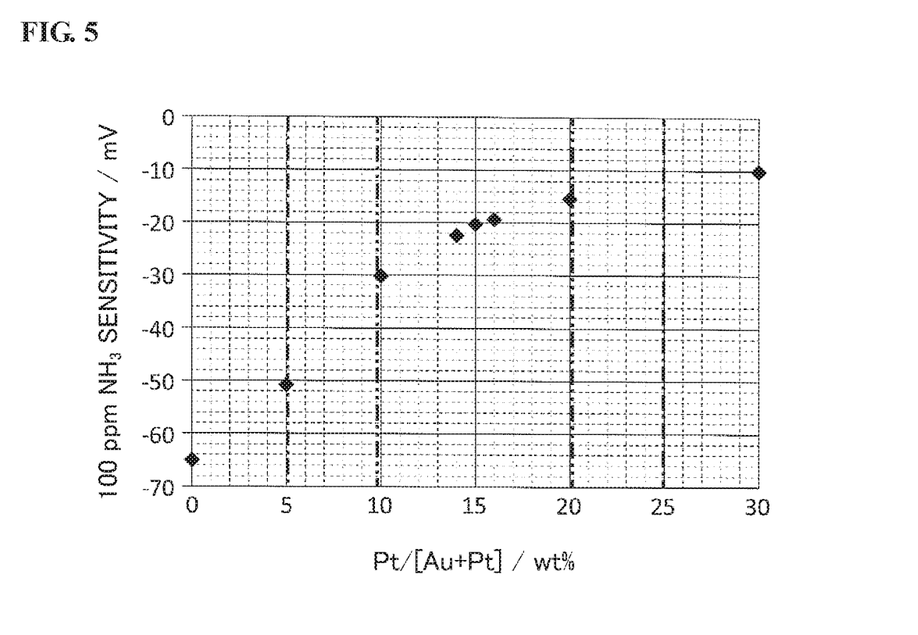
FIG. 5 is a graph showing a relationship between the metal composition and the $NH_3$ sensitivity of a first detection electrode of the first ammonia detection cell.
Figure 6:
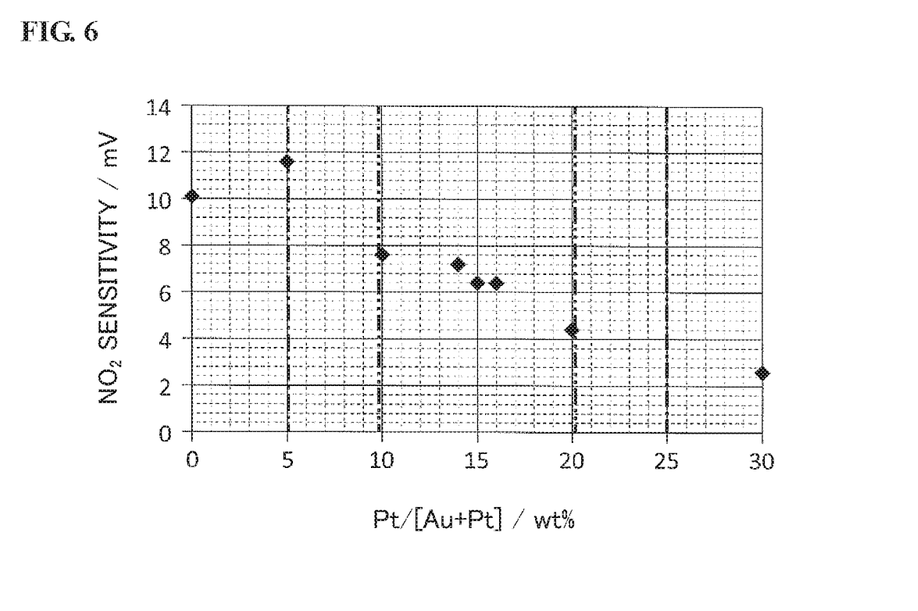
FIG. 6 is a graph showing a relationship between the metal composition and the $NO_2$ sensitivity of the first detection electrode.
Figure 7:
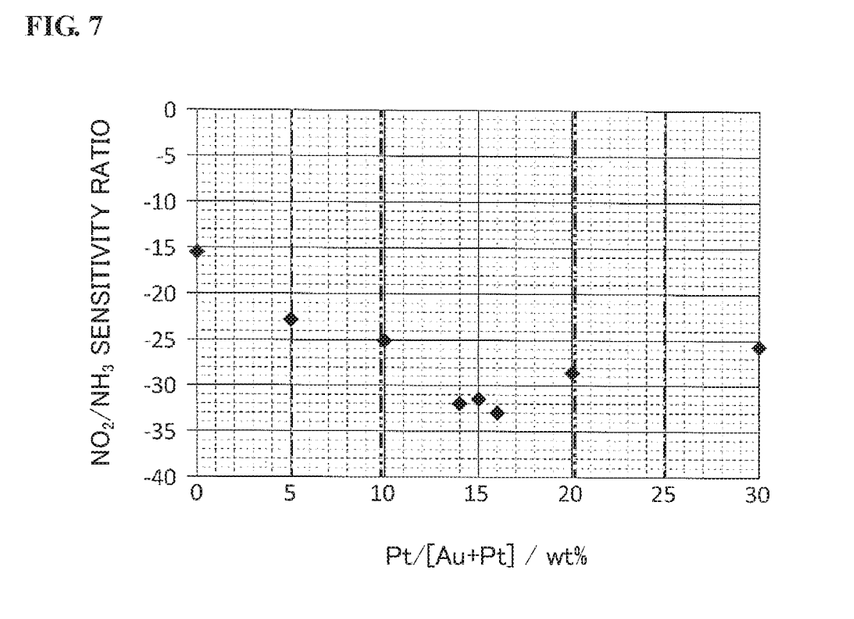
FIG. 7 is a graph showing a relationship between the metal composition and the $NO_2/NH_3$ sensitivity ratio of the first detection electrode.
Figure 8:
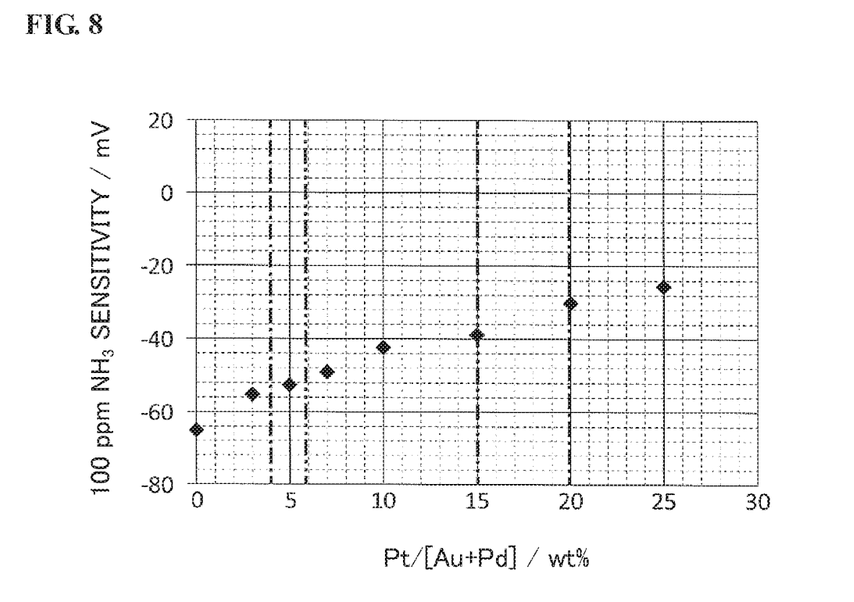
FIG. 8 is a graph showing a relationship between the metal composition and the $NH_3$ sensitivity of a second detection electrode of the second ammonia detection cell.
Figure 9:
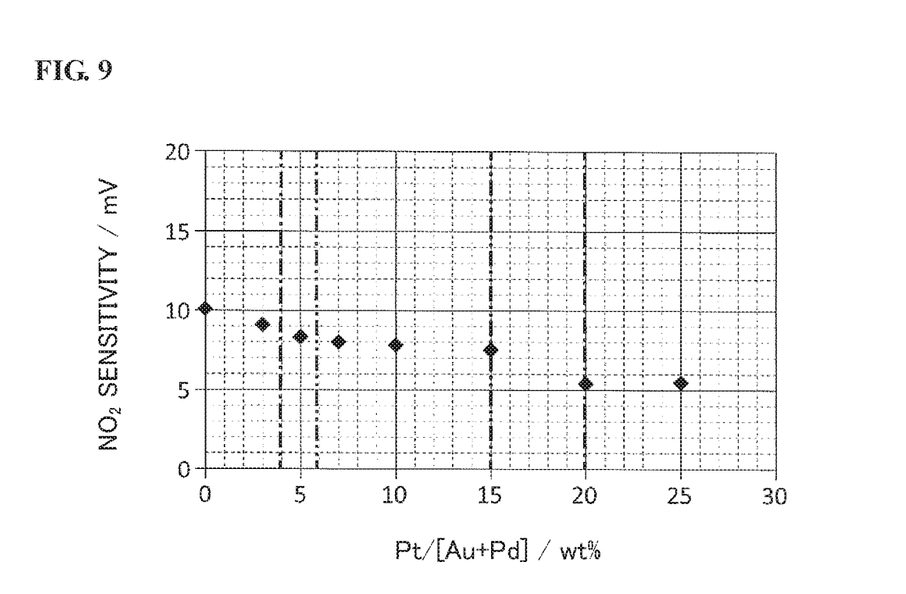
FIG. 9 is a graph showing a relationship between the metal composition and the $NO_2$ sensitivity of the second detection electrode.
Figure 10:
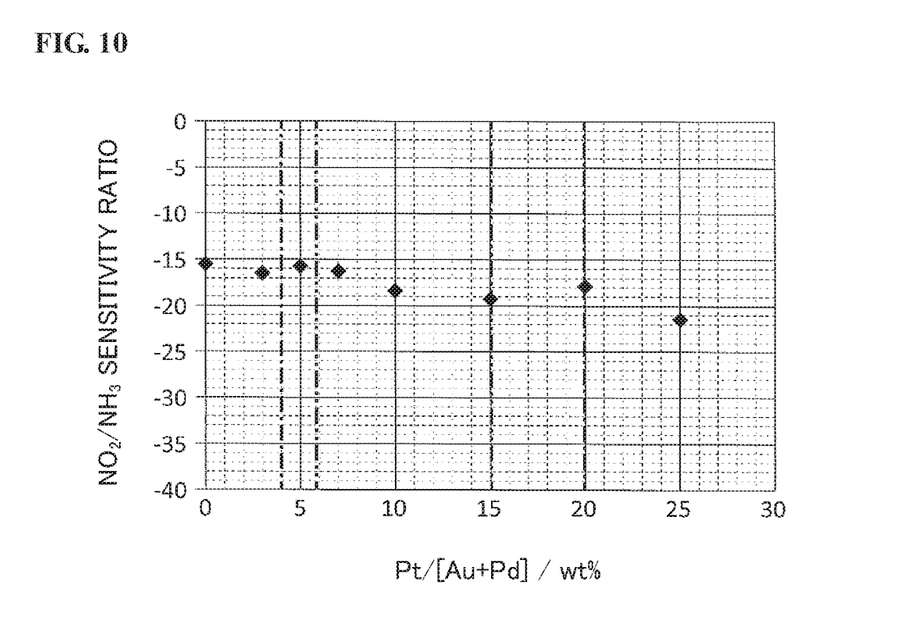
FIG. 10 is a graph showing a relationship between the metal composition and the $NO_2/NH_3$ sensitivity ratio of the second detection electrode.

In one example, the metal composition of the first detection electrode 42bx consists of an alloy phase of Au and Pt; and the metal composition of the second detection electrode 42by consists of an alloy phase of Au and Pd. FIG. 5 is a diagram showing a relationship between the weight percentage ratio Pt/(Au+Pt) and $NH_3$ sensitivity of the first detection electrode 42bx. FIG. 6 is a diagram showing a relationship between the weight percentage ratio Pt/(Au+Pt) and $NO_2$ sensitivity of the first detection electrode 42bx. FIG. 7 is a diagram showing a relationship between the weight percentage ratio Pt/(Au+Pt) and $NO_2/NH_3$ sensitivity ratio of the first detection electrode 42bx. The $NO_2/NH_3$ sensitivity ratio of FIG. 7 is determined from FIGS. 5 and 6. Similarly, FIG. 8 is a diagram showing a relationship between the weight percentage ratio Pd/(Au+Pd) and $NH_3$ sensitivity of the second detection electrode 42by. FIG. 9 is a diagram showing a relationship between the weight percentage ratio Pd/(Au+Pd) and $NO_2$ sensitivity of the second detection electrode 42by. FIG. 10 is a diagram showing a relationship between the weight percentage ratio Pd/(Au+Pd) and $NO_2/NH_3$ sensitivity of the second detection electrode 42by. The $NO_2/NH_3$ sensitivity of FIG. 10 is also determined from FIGS. 8 and 9.

It is apparent from FIGS. 7 and 10 that the ammonia detection cells 42x and 42y ensure sufficient outputs for practical use when the weight percentage ratio Pt/(Au+Pt) of the first detection electrode 42bx is in the range of 5 to 25 wt % and the weight percentage ratio Pd/(Au+Pd) of the second detection electrode 42by is in the range of 4 to 20 wt %. The weight percentage ratio Pt/(Au+Pt) of 5 to 25 wt % corresponds to a weight ratio Pt/(Au+Pt) ratio of 0.05 to 0.25; and the weight percentage ratio Pd/(Au+Pd) of 4 to 20 wt % corresponds to a weight basis ratio Pd/(Au+Pd) of 0.04 to 0.20. In these composition ranges, the metal compositions of the first and second detection electrodes 42bx and 42by are high in melting point so that the protection layer 23g can be formed by high-temperature sintering without causing evaporation of the detection electrode 42bx, 42by during the sintering.

It is further apparent from FIGS. 7 and 10 that the ammonia detection cells 42x and 42y ensure more sufficient outputs for practical use when the weight percentage ratio Pt/(Au+Pt) of the first detection electrode 42bx is in the range of 10 to 20 wt % and the ratio Pd/(Au+Pd) of the second detection electrode 42by is in the range of 6 to 15 wt %. The weight percentage ratio Pt/(Au+Pt) of 10 to 20 wt % corresponds to a weight ratio Pt/(Au+Pt) ratio of 0.10 to 0.20; and the weight percentage ratio Pd/(Au+Pd) of 6 to 15 wt % corresponds to a weight basis ratio Pd/(Au+Pd) of 0.06 to 0.15.

As described above, the gas sensor 200A is provided with the ammonia sensor part (ammonia sensor element) 42 using a novel ammonia detection technique. In particular, the melting points of the detection electrodes 42bx and 42by are raised when the metal composition of the detection electrode 42bx, 42by contains Au in combination with a metal higher in melting point than Au and capable of alloying with Au. This allows adoption of high-temperature sintering for the formation of the protection layer 23g and thereby makes it possible to ensure the strength and poisoning resistance of the protection layer 23g.

2. Modification Examples

Although the present invention has been described with reference to the above embodiment, the above embodiment is not intended to limit the present invention thereto. Various changes and modifications can be made to the above embodiment without departing from the scope of the present invention.

Figure 11:
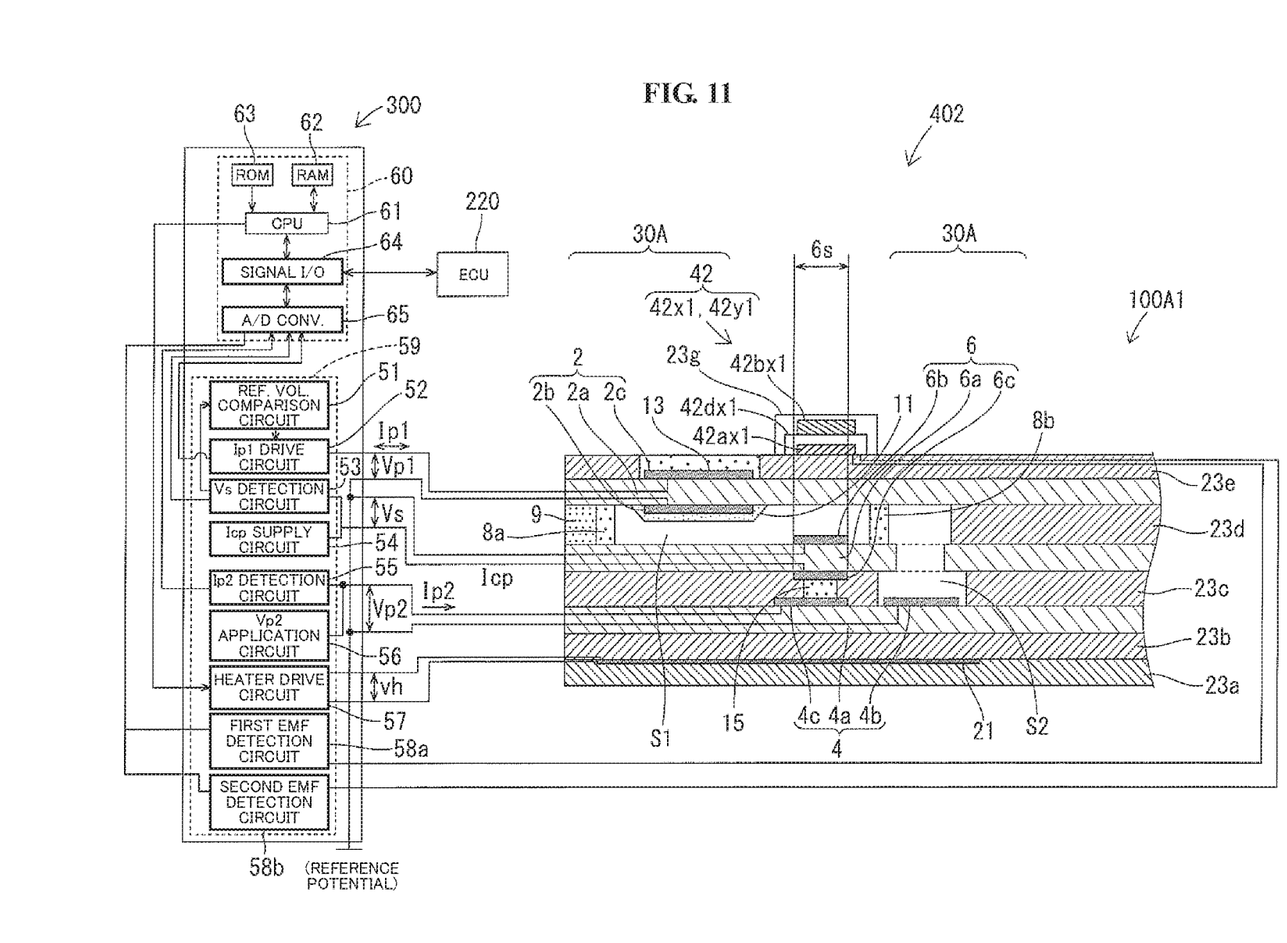
FIG. 11 is a block diagram of a multi-gas sensor apparatus with a multi-gas sensor according to another embodiment of the present invention and a sensor controller.

In the above embodiment, the ammonia detection cells 42x and 42y are arranged on the outer surface of the insulating layer 23a (i.e. on one main surface of the NOx sensor part 30A). However, the arrangement of the ammonia detection element 42x and 42y is not limited to this embodiment. As a modification of the embodiment, there may be provided a multi-gas sensor apparatus 402 with a multi-gas sensor unit 100A1 in which ammonia detection cells 42x1 and 42y1 are arranged on the outer surface of the insulating layer 23e (i.e. on the other main surface of the NOx sensor part 30A) as shown in FIG. 11. The multi-gas sensor apparatus 402 of FIG. 11 is structurally similar to the multi-gas sensor apparatus 400 of FIG. 2, except for the configuration of the multi-gas sensor unit 100A1 due to different positions of the ammonia detection cells 42x1 (including a first reference electrode 42ax1, an ammonia detection electrode 42bx1 and a solid electrolyte body 42dx) and 42y1. In this modification example, like parts and portions are designated by like reference numerals to omit repetitive description thereof.

The entire contents of Japanese Patent Application No. 2018-059399 (filed on Mar. 27, 2018) are herein incorporated by reference. The scope of the present invention is defined with reference to the following claims.

What is claimed is:

1. An ammonia sensor element for detecting ammonia in a gas under measurement, comprising two mixed-potential-type ammonia detection cells that respectively include first and second ammonia detection electrodes, wherein the first ammonia detection electrode has a metal composition containing Au as a predominant component, wherein the second ammonia detection electrode has a metal composition containing Au as a predominant component, wherein the metal compositions of the first and second ammonia detection electrodes are different from each other, wherein the metal composition of the first ammonia detection electrode contains Au as a first metal element and a second metal element different from the first metal element, and wherein the metal composition of the second ammonia detection electrode contains Au as the first metal element and a third metal element different from the first and second metal elements.

2. The ammonia sensor element according to claim 1, wherein the ammonia detection cells are integrally covered with a protection layer or separately covered with protection layers, wherein the metal composition of the first ammonia detection electrode contains a metal having a melting point higher than that of Au and capable of alloying with Au, and wherein the metal composition of the second ammonia detection electrode contains a metal having a melting point higher than that of Au and capable of alloying with Au.

3. The ammonia sensor element according to claim 2, wherein the metal composition of the first ammonia detection electrode consists of an alloy phase of Au and Pt, and wherein the metal composition of the second ammonia detection electrode consists of an alloy phase of Au and Pd.

4. The ammonia sensor element according to claim 3, wherein the metal composition of the first ammonia detection electrode has a weight ratio Pt/(Au+Pt) of 0.05 to 0.25, and wherein the metal composition of the second ammonia detection electrode has a weight ratio Pd/(Au+Pd) of 0.04 to 0.20.

5. The ammonia sensor element according to claim 4, wherein the metal composition of the first ammonia detection electrode has a weight ratio Pt/(Au+Pt) of 0.10 to 0.20, and wherein the metal composition of the second ammonia detection electrode has a weight ratio Pd/(Au+Pd) of 0.06 to 0.15.

6. A gas sensor, comprising the ammonia sensor element according to claim 1.

7. The gas sensor according to claim 6, wherein the gas sensor is in the form of a multi-gas sensor comprising a NOx sensor part that measures the concentration of nitrogen oxides in the gas under measurement.

* * * * *